United States Patent [19]

Mann

[11] Patent Number: 5,718,894
[45] Date of Patent: Feb. 17, 1998

[54] FORMULATION AND USE OF MICROORGANISMS IN TREATING LIVESTOCK

[75] Inventor: Stephen P. Mann, Harston, United Kingdom

[73] Assignee: Biotal Ltd., Cardiff, United Kingdom

[21] Appl. No.: 256,657

[22] PCT Filed: Jan. 13, 1993

[86] PCT No.: PCT/GB93/00065

§ 371 Date: Jul. 13, 1994

§ 102(e) Date: Jul. 13, 1994

[87] PCT Pub. No.: WO93/13786

PCT Pub. Date: Jul. 22, 1993

[30] Foreign Application Priority Data

Jan. 16, 1992 [GB] United Kingdom .................. 9200891

[51] Int. Cl.⁶ .................. A61K 35/74; A23K 1/16
[52] U.S. Cl. .................. 424/93.3; 424/93.45; 435/42
[58] Field of Search .................. 435/42; 424/93.45, 424/93.3

[56] References Cited

U.S. PATENT DOCUMENTS

| | | | |
|---|---|---|---|
| 3,875,306 | 4/1975 | Alstrom | 426/61 |
| 4,362,710 | 12/1982 | Watanabe | 424/442 |
| 4,808,417 | 2/1989 | Masuda | 426/2 |
| 4,946,791 | 8/1990 | Manfredi et al. | 435/854 |
| 4,980,164 | 12/1990 | Manfredi et al. | 424/93.45 |
| 4,999,193 | 3/1991 | Nguyen | 424/93.46 |
| 5,093,121 | 3/1992 | Kvanta et al. | 424/93.44 |
| 5,179,020 | 1/1993 | Herman et al. | 435/854 |
| 5,256,425 | 10/1993 | Herman et al. | 424/93.45 |
| 5,360,730 | 11/1994 | Orndorff et al. | 435/172.1 |
| 5,374,425 | 12/1994 | Porter | 424/93.45 |

FOREIGN PATENT DOCUMENTS

| | | |
|---|---|---|
| 0 208 818 | 1/1987 | European Pat. Off. |
| 0 290 410 | 11/1988 | European Pat. Off. |
| 0 397 227 | 11/1990 | European Pat. Off. |
| 1040278 | 8/1966 | United Kingdom. |
| WO 89/11858 | 12/1989 | WIPO. |

*Primary Examiner*—Herbert J. Lilling
*Attorney, Agent, or Firm*—Oliff & Berridge, P.L.C.

[57] ABSTRACT

For therapeutic use, and particularly for promoting growth or weight gain in livestock under intensive husbandry, a formulation comprises a first microorganism capable of producing lactic acid in the gastrointestinal tract of the animal and a second microorganism capable of producing a bactericide to which the microorganisms are resistant. The formulation may also comprise the means for digesting fiber and/or lactoperoxidase.

14 Claims, No Drawings

FORMULATION AND USE OF MICROORGANISMS IN TREATING LIVESTOCK

FIELD OF THE INVENTION

This invention relates to a formulation of microorganisms suitable for administration to an animal, for therapeutic purposes or to promote growth, weight gain or another desirable aim in commercial livestock.

BACKGROUND OF THE INVENTION

In the production and growth of all animals, it is possible to identify periods of vulnerability to infection of the gastrointestinal tract (GIT), e.g. parturition and weaning, and other periods of a traumatic nature that are generally referred to as "stress". During these periods of change, the first manifestation of deleterious effects occurring is usually a loosening of bowel function and diarrhoea. In extreme cases, such symptoms can lead to the onset of dehydration, and ultimately death. The effect of sub-acute infections is a marked check in the animals' growth, that can even lead to a loss in weight.

In the wild, although the periods of "stress" occur, they prove less traumatic, as seen by the reduced occurrence of the symptoms described above. By contrast, under conditions of normal and intensive husbandry, the effects of "stress" may be both intensified and prolonged, and additional traumas such as maternal separation, transport, human handling and unusual environments may be introduced.

In current practice of intensive husbandry in pigs, antibiotics such as tylosin are added to the animal feed to prevent or reduce GIT infections. Growth of the animals is thus promoted, when compared with untreated controls, by preventing the onset of the debilitating effects of the GIT infections. The addition of copper to the feed is also common practice, but the mechanism of action is uncertain. It has however been shown that the presence of copper, under certain conditions, can lead to the production of $H_2O_2$, which is also produced by the action of bacteria in the GIT.

SUMMARY OF THE INVENTION

A novel formulation of microorganisms, according to the present invention, is both capable of producing lactic acid in the GIT and also of producing (directly or indirectly, in situ), a bactericide to which the microorganisms in the formulation are resistant.

DESCRIPTION OF THE INVENTION

The microorganisms in the novel formulation severally and collectively produce compounds and enzymes that encourage the establishment of a predominant and benign flora in the GIT of mammalian, avian and piscine species. The establishment of such a flora prevents the onset of those gastrointestinal diseases caused by the establishment of an alternative and deleterious flora in the intestine.

The mode of action of these bacteria is to produce antimicrobial enzymes, bactericides and bacteriostats which prevent the establishment of bacteria other than those administered. This by contrast to the disadvantages associated with current techniques for achieving the same aims, i.e. by using a combination of aseptic husbandry with the addition of antibiotics and high concentrations of copper to animal feeds.

The principles described herein are applicable to a wide variety of animal species and commercial practices. The establishment of appropriate benign flora may be considered in the GIT of many animals that are used for the commercial production of meat, milk and fish. In addition, since an object of the invention is to improve the health and well-being of animals in general, its use and applicability can be extended to draught animals, companion animals and humans.

A first microorganism in the novel formulation has the capability of producing lactic acid in the GIT. This microorganism is, for example, of the genus Lactobacillus or Enterococcus. Either or both genera may be used; they are distinguished by their ability to utilise sugars such as glucose or lactose or, in the case of Enterococcus, to utilise starch, to produce lactic acid and thus reduce the local pH. The choice of microorganism will depend on the locus at which it is desired to give the desired effect; for example, microorganisms of the genus Lactobacillus produce lactic acid at a more acid pH than those of the genus Enterococcus. Species of each of these genera that may be used are *L. kasei*, *L. aminosum*, *L. fermentum*, *E. faecalis* and *E. faecium*. A mixture of more than one of each such microorganism may be used.

A second microorganism that is used is capable of producing a bactericide, e.g. by providing a substrate for lactoperoxidase, to produce peroxide. The other microorganisms in the formulation should be resistant to that bactericide. Such a bactericide is capable of combating microorganisms that are the positive agent of enteric disorders, e.g. *Staphylococcus aureus*, *E. coli* and *Salmonella*.

The use of microorganisms ensures that the desired effect is produced locally. The various microorganisms in the formulation should be compatible, e.g. capable of growing together. Fast growth at the locus of action is desirable. The microorganisms may be selected for various characteristics, e.g. resistance to commercial antibiotics and also bile acids, that make them suitable for their intended use.

The formulation may be supplemented with enzymes, or microorganisms producing enzymes, which digest fibre. Such enzymes include arabinase and xylanase. Another useful enzyme is glucose oxidase, to produce (additional) peroxide. In addition, enzymes or biocatalysts producing free radicals from peroxide, e.g. lactoperoxidase, may be added to supplement or replace the natural enzymes found in milk. Such free radicals have a disinfectant effect on some organisms that are generally not effective on the selected strains in vivo.

A formulation of the invention can be used initially with the administration of conventional antibiotics. However, its continuing administration allows the amount of tylosin, virginiamycin or similar antibiotic to be reduced, and the requirement for copper in animal feeds can also thus be reduced or prevented. The microorganisms that are used in the novel formulation are selected for their ability to produce compounds such as bacteriocins and other such compounds in sufficient quantities to prevent the establishment of the deleterious bacteria in the GIT (e.g. *E. coli*, Salmonella etc.). The bacteria can be isolated from wild or cross-bred animals kept under non-intensive husbandry conditions. The quantities of the antimicrobial produced by these bacteria, however, remains small compared with the concentrations of antibiotics currently added to animal feeds. The possibility of the emergence of resistant strains is therefore much reduced. Further, by using a number of such compounds, the possibility of undesirable bacteria establishing resistance to a single agent is reduced.

Anti-bacterial compounds in this context will cover a wide range of compounds and are not confined to those generally referred to as antibiotics, though the production of antibiotics in vivo is part of the synergic effects that may be observed. The anti-bacterial compounds include those that produce bacteriocins, lactic acid, peroxide and enzymes. In addition, enzymes may be added to the formulation prior to ingestion, to enhance the establishment of the bacteria. Thus the inclusion of amylase and/or peroxidase will assist in the establishment of the desired flora.

The establishment of the desirable and benign flora depends on the selection of complementary species and strains that will establish themselves in most if not all of the ecological niches that are to be found in the GIT. Such ecological areas could under other conditions harbour undesirable organisms. The selected microorganisms must, however, be sufficiently compatible to be specific to a particular environment, or resistant to the metabolic products of the other organisms to be used.

The desired flora must be established in competition with an already established flora. In the GIT of young animals, it is necessary to saturate as far as is possible the environment of the young animal with the desired flora. To this end, the formulation is fed to animals prior to parturition, following an intense course of administration lo of the formulation after administration of a course of antibiotics, or together with a compatible antibiotic. The administration of the formulation to the young animals, post-parturition, is preferably immediate and supplemented with a continuous administration with the feed. For this purpose, and in consideration of the processes of preparation of commercial animal feeds, strains of the organisms are preferably selected or produced that are resistant to the temperatures, e.g. 45° C. or more, encountered during the manufacturing and pelleting processes.

By way of illustration only, the invention will now be described in terms of a formulation suitable for use in pigs. The intention is to remove synthetic antibiotics and copper from feed. It derives from observations that the flora in the GIT of wild-type pigs, kept under non-intensive conditions of husbandry, varies with age, and that a number of species tend to dominate during the stages of development. Three genera are found consistently: Lactobacilli, Enterococci and Bacilli. Of these, the *E. faecalis* and *E. faecium* predominate during the early stages of the animals' life. Lactobacilli are present from the earliest stages of life through to adulthood. Bacilli are present throughout, but become particularly numerous with the onset of an adult diet.

This flora is notable for a number of reasons:

1. The bacteria all grow at low values of pH and all produce acid (usually but not exclusively lactic acid).
2. The Bacilli in particular produce anti-bacterial compounds (e.g. bacitracin and polymyxin) while the Enterococci appear to be resistant to the release of such compounds (particularly bacitracin).
3. All these bacteria can use lactose as a carbon source and therefore have the ability to predominate in the presence of a milk diet containing lactose.
4. In addition, the organisms as a whole can use a wide variety of carbon sources including structural (plant) polysaccharides which enables them to colonise the GIT over all stages of the animals' life.
5. The Lactobacilli and the Streptococci all produce peroxide which in combination with the lactoperoxidase in milk and saliva produces a natural bactericide. This should permit the removal of copper from the diet since one putative mechanism for the copper in the diet is the production of peroxide in the presence of ascorbic acid.

EXAMPLE

A formulation for use in pigs (but also other animals, e.g. man) is composed of four strains selected to show heat tolerance. Each strain is used at $10^9$ cfu/g.

|  | Growth at (°C.) | Resistant to (°C.) |
| --- | --- | --- |
| Lactobacillus | 50 | ? |
| *Enterococcus faecalis* | 45–50 | 60–65 |
| *Enterococcus faecium* | 45–50 | 60–65 |
| *Bacillus licheniformis* | 55–60 | spores 110° C. |

All strains are capable of anaerobic growth and of utilising lactose and, except for the *E. faecium*, sucrose. Two strains of Bacillus are used, each capable of utilising arabinose, starch, pectin and araban, of growth on beet pulp, of inhibiting *S. aureus*, Salmonella and *E. coli*, and of producing xylanase and arabinofuranase, and each resistant to the antibiotics bacitracin, virginiamycin and tylosin (to a degree), and to porcine bile extract. They each grow in the relatively high pH of the hind gut.

The other strains (Lactobacillus and Enterococcus) are producers of lactate and all are resistant to porcine bile extract and the antibiotics given above, except that Lactobacillus and *E. faecalis* strains may not be resistant to bacitracin. This apparent disadvantage is countered by the practical aspect that these strains grow at low pH and are not affected by bacitracin in the upper intestine, where the production of lactate is important.

The formulation may be supplemented by the addition of one or more enzymes selected from peroxidase, lipase, glucose oxidase, amylase and glucanase.

In initial trials, this formulation has been shown to allow the replacement of antibiotic feed additives and copper in pigs, while mimicking the beneficial effects of such additives. A reduction in the presence of harmful microorganisms, as evidenced by the absence of the MMA syndrome, was observed.

I claim:

1. A method for the promotion of growth or weight gain in a farm animal, comprising administering to the animal a first bacterium capable of producing lactic acid in the gastrointestinal tract of the animal and a second bacterium capable of producing a bactericide to which the bacteria are resistant, wherein said second bacterium is a Bacillus.

2. A method according to claim 1, wherein the first bacterium is a Lactobacillus.

3. A method according to claim 1, wherein the first bacterium is an Enterococcus.

4. A method according to claim 1, which additionally comprises administering to the animal an agent that comprises lactoperoxidase.

5. A method according to claim 1, wherein each of the bacteria that are used is resistant to the antibacterial products of the other bacteria.

6. A method according to claim 1, wherein each of the bacteria that are used is resistant to synthetic antibiotics used to combat pathogens of the gastrointestinal tract.

7. A method according to claim 1, wherein the animal is a pig.

8. A formulation comprising a first bacterium capable of producing lactic acid in a gastrointestinal tract of an animal and a second bacterium capable of producing a bactericide to which the bacteria are resistant, wherein said second bacterium is a Bacillus, and an agent that comprises lactoperoxidase.

9. A formulation according to claim 8, wherein each component thereof is resistant to the antibacterial products of the other components.

10. A formulation according to claim 8, wherein each component thereof is resistant to synthetic antibiotics used to combat pathogens of the gastrointestinal tract.

11. A formulation according to claim 8, characterised by the ability to reduce the growth rates of harmful enteric bacteria.

12. The method according to claim 6, wherein each of the bacteria is resistant to synthetic antibiotics used to combat *E. coli*.

13. The formulation according to claim 10, wherein each component is resistant to synthetic antibiotics used to combat *E. coli*.

14. The formulation of claim 11, wherein said harmful enteric bacteria is selected from the group consisting of *E. coli*, Salmonella and Clostridia.

* * * * *